Figure 2:
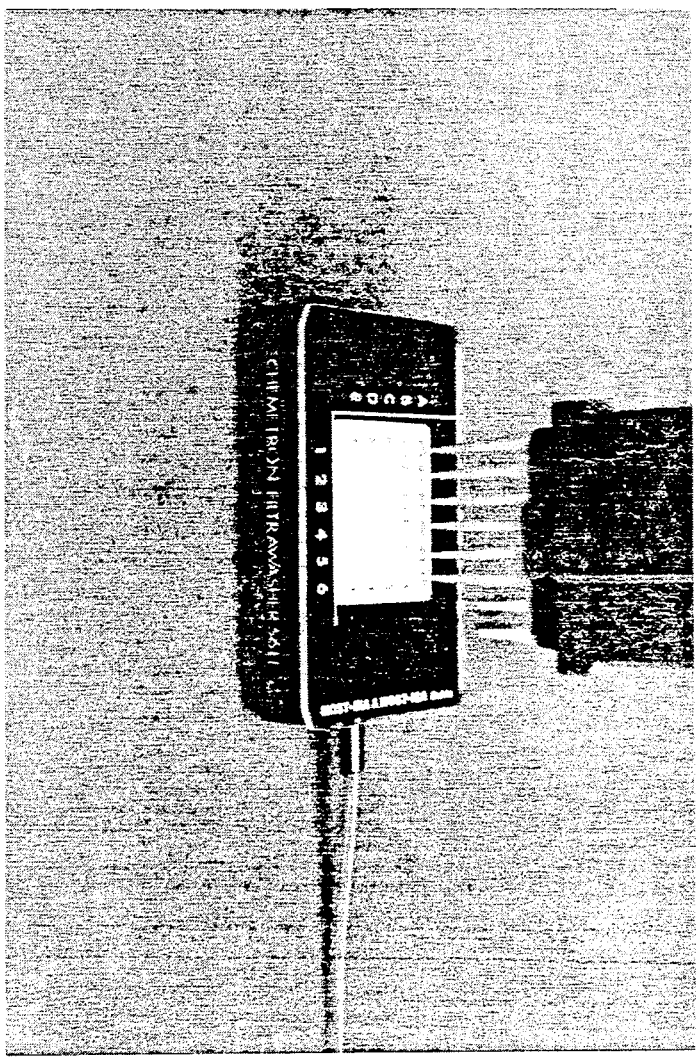

United States Patent [19]

Del Campo

[11] Patent Number: 4,990,442

[45] Date of Patent: Feb. 5, 1991

[54] ASSAY FOR AN ANALYTE ON A SOLID POROUS SUPPORT

[75] Inventor: G. B. Del Campo, Milan, Italy

[73] Assignee: Chemetron, Milan, Italy

[21] Appl. No.: 132,877

[22] Filed: Dec. 14, 1987

[30] Foreign Application Priority Data

Apr. 6, 1987 [IT] Italy .................. 19998 A/87

[51] Int. Cl.$^5$ ............... G01N 33/53; G01N 33/543; G01N 33/544; B01D 39/00

[52] U.S. Cl. ............... 435/7.5; 210/500.3; 422/101; 435/174; 435/301; 435/7.92; 436/501; 436/518; 436/530; 436/823; 436/824; 530/810

[58] Field of Search ............... 422/101; 435/301, 810, 435/7, 174; 436/501, 530, 518, 809, 824, 823; 210/500.3; 530/810

[56] References Cited

U.S. PATENT DOCUMENTS

| | | | |
|---|---|---|---|
| 4,193,983 | 3/1980 | Ullman et al. | 436/829 |
| 4,391,904 | 7/1983 | Litman et al. | 435/7 |
| 4,493,815 | 1/1985 | Fernwood et al. | 422/101 |

FOREIGN PATENT DOCUMENTS

2099578 12/1982 United Kingdom .

OTHER PUBLICATIONS

Maggio, *Enzyme-Immunoassay*, CRC Press, Inc., Boca Raton, Fl., 167-178 (1980).
Schleicher & Schuell brochure, *Minifold*, 1981.
Bio-Rad Catalog, 1984, pp. 167-168.
Hawkes, Methods in Enzymology, Academic Press, Inc., New York, May 1986, pp. 484-491.

*Primary Examiner*—Esther L. Kepplinger
*Assistant Examiner*—Florina B. Hoffer
*Attorney, Agent, or Firm*—Elliot M. Olstein

[57] ABSTRACT

An assay for an analyte wherein sample is applied to a support capable of binding proteins by essentially only hydrogen bonding and fixed on the support. Analyte may be determined on the support by use of a suitable tracer. A preferred support is amphiphilic cellulose acetate. In an immunoassay, it is possible to determine analyte without use of a supported ("capture") antibody.

26 Claims, 2 Drawing Sheets

FIG-1

ASSAY FOR AN ANALYTE ON A SOLID POROUS SUPPORT

This invention relates to an assay and kit for determining various analytes, and more particularly, this invention relates to an assay and product for determining various analytes by use of a solid support.

There are a wide variety of assay procedures currently available for determining an analyte by so-called immunochemical or immunological procedures. In brief, one such assay involves supporting on a solid support, a binder which specifically binds the analyte and then contacting the supported binder with a sample which contains or is suspected of containing the analyte to thereby bind the analyte to the supported binder. The bound analyte is then detected by use of a suitable tracer, which is generally a ligand which recognizes the analyte and which is labelled with a detectable label. The presence and/or amount of analyte in the sample may then be determined by determining the presence and/or amount of tracer on the solid support. The tracer may be labelled with a variety of detectable labels, and in general, such detectable label is either a radioactive isotope or an enzyme.

The present invention is directed to providing an improved solid phase assay.

In accordance with one aspect of the present invention, there is provided an assay for determining analyte (qualitatively and/or quatitatively) wherein a sample containing analyte is contacted with a solid porous support which is capable of reversibly binding analyte by essentially only hydrophobic bonding (hydrogen bonding) followed by determining the analyte on the solid support.

In accordance with another aspect of the present invention, there is provided an assay for determining analyte (qualitatively and/or quantitatively, preferably quantitatively) by contacting a sample containing or suspected of containing an analyte with a solid support wherein the solid support is an amphiphilic support capable of reversibly binding analyte by essentially only hydrophobic bonding (hydrogen bonding), and then determining analyte on the support.

In accordance with a preferred aspect of the present invention, the amphiphilic support (amphiphilic means that the support has both hydrophobic and hydrophilic properties) reversibly hydrophobically binds analyte to the support, whereby materials which are not "fixed" on the support may be removed from the support. The support is one which is capable of bonding or binding analyte by hydrophobic or hydrogen bonds, without any essential bonding or binding of the analyte to the support by covalent of ionic bonds, and in accordance with this aspect of the present invention, analyte may be bonded to or supported on the solid support without the use of a capture binder or antibody.

As hereinabove indicated, the solid support is a porous support which is amphiphilic, and which does not bind proteins and haptens by ionic or covalent bonds. Thus, in essence, the porous support is one which is both hydrophilic and hydrophobic (includes polar and non-polar groups) and has properties such that there is essentially no ionic or covalent bonds with proteins and haptens. Such a porous support may be produced by modifying a hydrophilic support to impart sufficient hydrophobicity thereto to permit hydrogen bonding of analyte to the support. Thus, for example, U.S. Pat. No. 4,158,683 discloses a hydrophilic porous support formed from cellulose acetate (cellulose diacetate). Such support may be modified to provide an amphiphilic support (one having both hydrophobic and hydrophilic properties) by treating the support with aqueous sodium chloride; for example, an aqueous solution containing from 0.95 to 4 molar sodium chloride. Alternatively, such cellulose acetate support may be imparted with hydrophobic properties by adding a hydrophobic compound to the materials used in forming the gel in an amount sufficient to impart hydrophobic properties. Such treatment imparts sufficient hydrophobicity to provide for hydrogen bonding, without increasing the hydrophobicity to a value which prevents wetting of the support. Thus, for example, a long chain fatty alcohol such as stearyl alcohol may be added to the materials used in forming the gel in order to provide an amphiphilic cellulose acetate support. The amphiphilic cellulose acetate support may be stored in a wet state; e.g., in an aqueous sodium chloride solution (0.15 to 4M) including 5% methanol. These and other amphiphilic supports should be apparent to those skilled in the art from the teachings herein. Such cellulose acetate supports which are rendered hydrophobic are often called aqueous gels.

In an assay procedure using an immunoassay technique (the term "immunoassay technique" also refers to assays which employ natural binders, sometimes referred to as protein binding assays), the amphiphilic support is contacted with the sample which contains or is suspected of containing the analyte. As a result of the hydrophobic properties of the support, proteins and haptens (including the analyte) in the sample are non-specifically bound to the support by hydrophobic binding.

Such materials are reversibly bound to the amphiphilic porous support (in the absence of "fixing" the materials may be washed from the support), and the analyte of interest must be "fixed" to the support for detection thereon. The term "fixed" means that the material on the support remains on the support even when the support is subjected to conditions which break the hydrophobic bonds.

In one embodiment, such analyte is "fixed" to the porous support by immunoreaction with a binder for the analyte (which may be the tracer used in the assay) to immunoprecipitate the analyte.

In another embodiment, such analyte is "fixed" to the solid support by the use of a fixative; for example, a fixative used in immunohistochemistry. Such fixatives are known in the art; e.g., formalin.

In the case where tracer has not been previously added, the solid support is contacted with a tracer which is comprised of a labeled ligand which is bound by the analyte or by a compound bound to the analyte.

The tracer which is not bound directly or indirectly to the analyte, although hydrophobically bound to the support, is not fixed to the support, whereby such unbound tracer may be washed or eluted from the support by breaking the hydrophobic bonds whereby the tracer which remains on the support is a measure of analyte (qualitative or quantitative).

More particularly, by fixing analyte on the support, any tracer which is directly or indirectly bound to the analyte is also fixed to the support. Since, as hereinabove noted, proteins and haptens, in the absence of fixing, are reversibly bound to the support by hydrogen bonding, tracer which is not bound directly or indirectly to the fixed analyte, may be eluted or washed from the support by disrupting or breaking such hydrogen bonds. Such bonds may be broken by the use of eluting solutions of a type employed for breaking hydrophobic bonds in protein chromatography, for example, an aqueous solution of an ionic detergent; buffered alkanol preferably about pH 7.2, etc.

The analyte may be fixed to the porous support by an immunoreaction, which in a direct assay format, is an immunoreaction between the analyte and tracer. In an indirect assay format, the analyte may be immunoreacted with a compound which immunoreacts with analyte which compound may be a binder for the analyte or a binder for the analyte coupled to a ligand. In the indirect format, the complex of the analyte with either a binder or a coupled compound of the type hereinabove described, is then contacted with a tracer which is bound by the compound (binder or coupled compound) bound to the analyte.

Unbound tracer (tracer not bound directly or indirectly to the analyte on the support) may then be eluted from the support in that unbound tracer is not "fixed" on the support, whereby the presence and/or quantity of tracer on the support is a direct measure of analyte.

In the case where analyte is fixed on the support by specific immunobinding, other proteins and haptens which were originally hydrophobically bound to the support are eluted from the support with unbound tracer.

In the case where analyte is fixed on the support by the use of a fixing agent; for example, of the type used in immunohistochemistry, proteins and haptens in addition to the analyte of interest, are also fixed to the support; however, tracer will only bind directly or indirectly to the analyte of interest, whereby determination of the tracer permits determination of analyte.

Thus, in accordance with an aspect of the present invention, the first step in the assay is contacting a solid, porous support of the type hereinabove described with sample containing, or suspected of containing, the analyte of interest. The sample may be in a wide variety of forms, such as, for example, serum, sputum, spinal fluid, and other body fluids, or may be a sample indirectly derived from body fluids, etc. Proteins and haptens in the sample are reversibly hydrophobically bound to the porous support.

The next step in the assay is optionally a separate fixing step in order to fix proteins and haptens to the support. The separate fixing step may not be required if the analyte of interest is immunoprecipitated in a subsequent step.

In a direct assay, the next step is contacting the solid support which includes analyte thereon with a tracer which is comprised of a ligand, which is bound by the analyte of interest, labelled with a detectable label or marker. The ligand which is used in the tracer is dependent upon the analyte. If the analyte is an antigen or hapten, the ligand may be an antibody (monoclonal or polyclonal antibody) or a naturally occuring binder for the antigen or hapten. If the analyte of interest is an antibody, then the ligand of the tracer may be an antigen or an antibody raised against the antibody analyte of interest, which antibody may be either a monoclonal or a polyclonal antibody.

The ligand of the tracer is labeled with a detectable label or marker, and any one of a wide variety of detectable labels or markers may be employed. For example, the detectable label or marker may be an enzyme, a fluorescent compound, an absorbing dye, a radioactive isotope, etc. The selection of a suitable detectable label or marker is deemed to be within the scope of those skilled in the art from the teachings herein.

In the case where the analyte is to be determined by an indirect procedure, the support is then contacted with a binder for the analyte or a coupled compound comprised of a binder specific for the analyte of interest and a ligand. The binder or binder portion of the coupled compound which is used is determined by the analyte of interest and may be an antigen, antibody (monoclonal or polyclonal antibody) or a naturally occurring binder for the analyte of interest. The ligand portion of the coupled compound may be any one of a wide variety of compounds which are generally employed for producing a coupled compound used in an indirect assay. For example, the ligand may be biotin, albumin, etc.

In the indirect assay, the tracer is comprised of a labeled binder for the compound which is bound to the analyte which is now fixed on the solid support. As hereinabove indicated, in the indirect assay, such compound may be a binder for the analyte or a binder for the analyte coupled to a ligand. If the compound is an uncoupled antibody, then the tracer may be a labeled antibody (monoclonal or polyclonal antibody) against such antibody. If such compound is a binder coupled to a ligand, then the labeled tracer may be a binder for the ligand portion of the coupled compound; for example, an antibody (monoclonal or polyclonal antibody). Thus, for example, if the ligand of the coupled compound is albumin, then the tracer may be labeled anti-albumin. Similarly, if the ligand of the coupled compound is biotin, then the tracer may be labeled anti-biotin or labeled avidin. The selection of a suitable tracer for an indirect assay is deemed to be within the scope of those skilled in the art from the teachings herein.

In accordance with the present invention, in performing a quantitative assay, the support should be a porous, amphiphilic support, which is capable of binding analyte of interest by essentially only hydrophobic bonds. If the assay is to be a qualitative assay, then the support need not necessarily be amphiphilic; however, the support should have hydrophobic properties to bind analyte of interest by essentially only hydrophobic bonds.

In accordance with a preferred aspect of the present invention, however, the support is an amphiphilic support, and the assay is a quantitative immunoassay. By using an amphiphilic support, it is possible to apply analyte to the porous support in a uniform manner; i.e., the protein present in the sample forms uniform spots on the support, rather than a plurality of rings.

In accordance with a particularly preferred embodiment, the solid support is in the form of a membrane having a thickness in the order of from 250 to 300 microns. Applicant has found that the use of a membrane of such thickness having the hereinabove noted properties provides for application of sample proteins as uniform spots on the membrane having small constant diameter sizes in the order of from 5 to 6 millimeters. The spots are formed uniformly irrespective of the concentration of protein or analyte of interest in the sample. In general, the porosity of the membrane is at least 300 Angstroms and may be as high as 3,000 Angstroms. The use of a thicker membrane provides for a smaller spot when applying sample to the membrane.

Although in a preferred embodiment of the present invention, analyte is placed on the support by hydrophobic bonding without requiring a trapping binder or antibody on the support, it is possible within the spirit and scope of the present invention to employ a support, as hereinabove described, in which trapping binder or antibody is placed on the support prior to addition of the sample. In such an embodiment, analyte of interest is specifically bound to the antibody or binder supported on such a solid support.

The present invention is also applicable to detecting analytes by assay procedures other than immunoassays. For example, in accordance with the present invention, it is possible to detect enzymes by standard chemistries. For example, a sample containing the enzyme of interest may be applied to the support, followed by "fixing" of proteins. Thereafter, a detection system which interacts with the enzyme is added to the support, and color determined on the support. For example, amylase may be "fixed" on the support as hereinabove described, and the amylase determined on the support by a detection system of a type known in the art.

The present invention is also applicable to determining proteins, such as total immunoglobulins. In such an assay, the support is contacted with a sample, and then the support is contacted with an antibody mixture containing antibodies to the immunoglobulins, such as a mixture of anti IgG, IgA, IgM, etc. The use of such an anti-serum mixture fixes total immunoglobulins to the support.

Thereafter, the support is washed to remove remaining unfixed proteins, followed by addition of a suitable protein stain, which functions as a tracer to detect bound protein. Any one of a wide variety of stains may be used, and as representative examples thereof, there may be mentioned green lissamine, Coomassie, gold stain, etc.

In some cases, it may be possible to add a labeled binder for the analyte of interest to a solution containing the analyte, followed by addition of the solution to a support of the type hereinabove described wherein proteins and haptens are reversibly bound by essentially only hydrogen bonding. As a result of the immunobinding of labeled binder and analyte, the resulting complex is "fixed" on the support and any unbound labeled binder and other proteins in the sample may be eluted from the support. The label may then be detected to determine analyte. Such methodology is also applicable to an indirect method; i.e., forming in solution an immunocomplex of analyte of interest and binder therefor; apply the solution to a support of the type hereinabove described; applying labeled binder for the binder member of the complex; eluting uncomplexed labeled binder from the support; and detecting label on the support to determine analyte.

In a preferred embodiment, as hereinabove indicated, the analyte does not form rings when deposited on the support; i.e., when it is deposited it is distributed uniformly over the support surface as a constant diameter spot, even if its concentration decreases to minimal values. As a result, sample diluents, when employed should be those which do not cause a circular mini-cromatography of the protein to be determined.

These diluents are chosen among those used for peptides and protein chromatography, the diluents being known as "slow eluents" of the protein to be determined and in some instances they contain 3% of Bovine Albumin facilitating a uniform distribution.

Advantageously, according to this invention, on the porous support one can simultaneously analyze a variety of samples which can be fixed on the membrane as spots in the same arrangement as the wells in conventional microtiter plates. To accomplish this, the analytic kit according to this invention may include a guide, for example a plastic one, of the type pictured in FIG. 1. The guide bears some sites according to an orderly arrangement corresponding, for example, to the above mentioned order of the wells in conventional microtiter plates. The preferred membranes and in particular the cellulose acetate membranes described herein are transparent or semi-transparent, whereby the sites marked on the guide are visible in transparence on the membrane, particularly when it is wet.

Alternatively, guides can be used in which analysis sites can be marked by perforations. As it will be explained later, these can also be used with a filtering device during a wash step according to this invention. Aliquots of fluid samples to be analyzed are placed in correspondency to the established sites indicated by the guides. Generally, aliquots from 3 to 5 microliters are used, having a protein concentration ranging from 0.01 ng (10 pg) to 1000 ng.

The aliquots are deposited by means of multiple micropipettes, such as the ones used on microtiter plates and they form uniform circular spots which, when the indicated aliquots are used, generally present a diameter to 5-7 mm.

In analysis methods which establish the fixing of a reaction product on a support (product of reaction of the proteins to be analyzed with the specific reagents), such a reaction takes place either before the deposit on the membrane, in liquid phase, or after placing the sample spot on the membrane. In the former case, aliquots of fluids containing the respective reaction products will be deposited on the membrane. In the latter, sample spots can first be deposited and then one can immerse the membrane in a reagent solution and incubate it as long as necessary for the reaction to occur.

Anyway, according to this invention, the reaction on the membrane between proteins and reagent, for example between an antigen Ag and Antibodies Abs specific for the reagent is immediate (a few minutes).

On the contrary, the reaction taking place in the microtiter wells on traditional plates, where a solid phase occurs during the reaction, have reaction times in the order of hours.

In the washing of the membrane on which the above mentioned spots have been fixed, in order to either remove any protein in the samples which could interfere with the analysis taking place at the time of final staining and/or removing of unbound tracer, an aspirating, filtering device of the type pictured in FIG. 2 can advantageously be used for the wash. One can use any filtering device with aspiration functions (for example a vacuum pump or water pump), bearing a filtertray fit to carry several microporous membrane cuts. With such a device, and type of support used in the procedure according to the invention, it is possible to accomplish very fast washings in the time range of 1-3 minutes, further reducing the length of analysis time.

With the above mentioned filtering devices under aspiration, it is possible to use the perforated guides. These guides, when placed on the filtertray with the membrane, under aspiration dig wells (or hollowed sites) on the membrane, in the same order as the wells on the microtiter plates. These hollowed sites allow deposits of immunoprecipitates obtained in the liquid phase of the Ag-Ab reaction.

Obviously, alternative washing systems can be used, for example immersing the membrane in tanks containing the washing solution.

If the marker of the tracer requires an additional treatment to provide for detection thereof; e.g., the use of a substrate for an enzyme marker, or if protein is to be stained to enable visualization thereof there is a final spot staining whose intensity is proportional to the concentration of analyte. Other than this, the spots are perfectly uniform and have the same diameter. Quantitative determination may be accomplished by a final reading of the color intensity of the spots, by means of a densitometer capable of simultaneously reading a variety of spots lines. To accomplish this, a densitometer for electrophoresis with a graphic printer can be used. A computerized densitometer of the type Multipolar (Chemetron) with 8 or 12 simultaneous reading and memorizing channels can be used also, which is capable of reading 12 lines of 8 spots each (96 spots) in a few seconds, expressing data in ng per spot.

The procedure according to this invention permits fast analyses.

The colored spots appearing on the membrane can be quantitatively read on the membrane, thus avoiding the emptying and transferring of stained samples from the wells to spectrophotometer cuvettes.

Finally, the analytic document related to a great variety of tests can be easily saved as a wet or dry membrane, together with the related quantitative photometric data under form of peaks as recorded by a densitometer.

The procedure according to this invention may be performed by means of analytic kits, ready to use. The kits come with the different reagents, solvents, diluents, washing solution, markers and chromogen specific for each type of protein to be analyzed, a microporous support according to this invention and a guide as above depicted.

Optionally the kit can also include a filtering device under aspiration as it has been explained before.

In the following examples immunoenzymatic, immunochemical and chemical methods are illustred, which can be performed by procedures and kit according to this invention.

EXAMPLE I

Preparation of Films of Cellulose Diacetate Aqueous Gel.

One hundred grams of 56% acetic acid cellulose acetate (i.e., cellulose diacetate) were dissolved under stirring for one night in a first mixture consisting of 300 cc of acetone and 200 cc of ethylene glycol monoethyl ether. Into this mixture kept under stirring, a second mixture containing 100 cc of acetone, 500 cc of ethylene glycol monoethyl ether and stearyl alcohol in an amount of from 0.4 to 0.8%, by volume, of the final volume of the swollen mass was dripped, taking care to avoid the formation of clots, thus obtaining a swollen mass. Agitation was maintained for about 1.5 hours while an amount of from 3 to 10% by weight based on the swollen mass, of formamide was added.

At the end of agitation, filtration was carried out and the mass was extended in the form of a film of required thickness.

This film was conditioned for about 30 minutes in low pressure surroundings in order to favor the evaporation of the acetone and was then immersed in water to substitute the remaining acetone and the ethylene glycol monoethyl ether. The material thus obtained was then cut and packaged in the humid state.

By this process translucent, white films are obtained. These films on exposure to air begin to dry after 10 minutes and their dimensions reduce after some hours by 10% with respect to the initial dimensions. These products have degree of gelatinisation controlled by the quantity of formide added to the mixture.

EXAMPLE II

The direct method can be employed for determination of proteins for which a peroxidase marked specific antiserum exists. For example, the method can be employed to determine urine $B_2$ microglobulin using an anti-$B_2$microglobulin HRP, antiserum peroxidase marked. A primary antiserum is not necessary to fix the antigen after the deposit. The antiserum solution contains a detergent (Tween 20) and an accellerant (PEG 6000).

METHOD

1. Samples and standards are directly diluted on the dilution plate, in order to have a standard range of 1-2-4-8-16-32 ng per 5 ul. For the samples the third dilution is preferred.

2. The membrane is dried with filter paper and it is placed on the guide. By semitransparence it is possible to see the markings where to deposit samples.

3. Samples and standards are deposited in correspondence to the established marks.

4. The membrane is transferred into an antigen fixing solution; the antigen fixatives are of the type used in immunohistochemistry, thus the antigens fix to the membrane. The spots are visible and it is therefore possible to check the correctness of the deposit.

5. The membrane is washed for 1 minute in distilled water and the wash is repeated twice for 3 minutes. The tank is emptied and 20-30 ml of antiserum diluent are poured in. It is equilibrated for 1 minute.

6. The membrane is incubated in 12 ml of the HRP-peroxidase antiserum (1:50 dilution) preferably at a temperature of 37° C., thus the Ab HRP-peroxidase binds to the antigen spots (the antiserum can be reused if the tank is saved under refrigeration).

7. The membrane is washed in PBS (Phosphate Buffered Saline, pH 7.2-7.4) for 1 minute.

8. The membrane is transferred on a filtering device of the type pictured in and washing solution is forced through the filter for 1-2 minutes or it is washed in tank for 30-40 minutes and at least 3 PBS separate washings.

9. The membrane is immersed in the chromogen just prepared, made on aminoethylcarbazole in ethanol, 15 ul $H_2O_2$ 30%, 20 ml of an acetate buffer, pH 5.2. After just 10-15 minutes, as soon as the white membrane surface starts turning to pink, the reaction must be blocked: the staining is discarded and the membrane is washed with water, 10. The membrane is scanned on densitometer (green filter) for the direct method described above to determine quantitatively urine $B_2$-microglobulin (48 tests), it is possible to use the following analytic test kit.

Kit Components

1 Cellogel (trademark) cellulose acetate gel membrane modified with stearyl alcohol to provide reversible hydrophobicity of the type described in Example I.
1 Plastic guide with 48 spots marks with numerical indication 1-6 and alphabetical A-H (see FIG. 2).

1 Antiserum anti-B₂-microglobulin HRP peroxidase
1 Standard with B₂-microglobulin, known titer
1 Sample and standard diluent for 48 tests including PBS and a staining indicator (Brominephenol Blue)
1 Antiserum diluent and membrane equilibrant (50 mil.), which includes PBS + Polyoxyethylensorbitanelaurate + Sodium Azide
1 Antigen fixating solution, including Glutaraldehyde 2% or Formalin in PBS
1 Envelope PBS (Phosphate Buffered Saline pH 7.2–7.4) dust for a 1 l of solution
1 Peroxidase developer (Aminoethylcarbazole in Ethanol, 1 ml $H_2O_2$, 20 ml of acetate buffer pH 5.2
2 Polycarbonate boxes (1 for incubation and 1 for staining or wash)
1 Plastic envelope to save used membrane

Extra Kit

A filtering and aspirating device, for example
Filtrawasher by Chemetron
A dilution plate with 48 wells
A Multipolar Densitomter (Chemetron)
Electric welder for polythene bags to save membrane with developed spots
Single pipette 0.5–10 ul or multipipette 0.5–50 ul
Transparency solution for Cellogel (Chemetron) for cleaning of the membrane.

EXAMPLE III

Indirect Immunoenzymatic Procedure with Biotin Avidin

Serum Ferritin has normal values which range from 0.012 ng/ul to 0.15 ng/ul. The answer with respect to the direct method therefore needs to be amplified about 100 times. Non-diluted sera are used, unless a severe increse of Ferritin concentration is expected (Thalassemia, sideroblastic anemia, solid tumors, malignant lymphoma and leucosis). The kit contains similar material to the one described for the direct method and in particular:

1 Prediluted rabbit primary antiserum anti-Ferritin
2 Swine biotinylated antiserum anti-rabbit Ig
3 AB complex (Avidin Biotin Peroxidase Complex)
4 Perforated guide for deposits on filtertray Sample containing Ferritin is applied to an amphiphilic cellulose acetate gel of the type described in Example I. Thereafter, primary antiserum is applied, followed by addition of the biotinylated antiserum. Thereafter, avidin labeled with peroxidase is applied and the peroxidase developed by use of a chromogen.

EXAMPLE IV

Immunochemical (non Enzymatic) Procedure with Direct Staining of Immunofixed Antigens.

The procedure illustrated is for determination of total Immunoglobulins. In this case the kit contains: Membrane as in Example I impregnated with a mixture primary antiserum anti IgG + IgA + IgM + kappa chain + lambda chain.
1 Guide to set down uniform spots.
1 Buffer solution to dilute samples (uniform spots former)
1 Standard calibrator containing 25-50-100-300-500-700 ng/5 ul of human Ig
1 Gold Stain staining solution or Coomassie BB 250R (ICI trademark)
2 Polycarbonate boxes
1 Plastic envelope to save used membrane The biological fluids samples are deposited on the membrane impregnated with primary antiserum where they are immunofixed following the Ag-Ab reaction. A washing step on filter follows, to eliminate proteins which have not reacted; afterwards it is possible to visualize using a protein stain. For spots from 30 to 900 ng it is possible to use Coomassie BB 250 R, whereas for spots from 5 to 50 ng Gold Stain can be employed.

EXAMPLE V

The method can be applied to determine Total Proteins (or a simple purified protein), which are deposited on a membrane as in Example I, and then fixed with a non-proteic reagent, for example trichloracetic acid. Visualization here occurs by staining, e.g., Coomassie or Gold Stain.

The present invention may be employed for determining a wide variety of analytes. As representative examples of such analytes, there may be mentioned: AFP; ferritin thyroglobulin; B₂-microglobulin; orosomucoid; Total IgE; IgB; IgA; IgM; IgD; CEA; ACTH; hCG; gastrin, prolactin; lactoferrin; anticardiolipin antibody; FSH; LH; TSH, etc. The selection of a suitable analyte is deemed to be within the scope of those skilled in the art from the teachings herein.

The present invention is particularly advantageous in that it is possible to determine various analytes without using a "capture" binder for the analyte, such as an antibody. The assay may be accomplished rapidly and a plurality of tests may be accomplished at the same time.

These and other advantages should be apparent to those skilled in the art from the teachings herein.

Numerous modifications and variations of the present invention are possible in light of the above teachings, therefore, within the scope of the appended claims the invention may be practiced otherwise than as particularly described.

I claim

1. An assay for determining analyte, comprising:
    contacting a support with sample containing an analyte, said support being essentially free of a binder which recognizes said analyte, said support being an amphiphillic support, said support reversibly binding protein by essentially only hydrogen bonding; fixing analyte on the support; subsequent to the fixing and prior to a subsequent determining of analyte, washing the support to remove proteins and haptens other than analyte fixed on the support; and determining analyte on the support.
2. The assay of claim 1 wherein sample is deposited on the support as a plurality of spaced sample portions.
3. The assay of claim 1 wherein prior to washing, analyte on the support is contacted with a tracer which binds directly or indirectly to analyte on the support.
4. The immunoassay of claim 3 wherein the analyte is fixed on the support by immunoreaction with the tracer.
5. The assay of claim 1 wherein analyte is fixed on the support by a fixing agent.
6. The assay of claim 1 wherein analyte is fixed on the support by an immunochemical reaction.
7. The assay of claim 6 wherein in the washing subsequent to fixing analyte on the support and prior to determining analyte proteins other than analyte which are reversibly bound to the support are eluted from the support by breaking hydrogen bonds.
8. The assay of claim 7 wherein the membrane is amphiphilic cellulose acetate.

9. The assay of claim 8 wherein sample is applied to the support as a plurality of sample portions spaced over the support surface.

10. The assay of claim 8 wherein the analyte is determined quantitatively.

11. The assay of claim 10 wherein the sample is applied to the support by use of a guide which spaces the sample portions as wells are spaced in a microtiter tray.

12. The assay of claim 6 wherein the support is cellulose acetate modified with a long chain fatty alcohol.

13. The assay of claim 1 wherein the analyte is a protein.

14. The assay of claim 1 wherein analyte is determined on the support by use of a labeled binder bound directly or indirectly to the analyte, and unbound labeled binder is eluted from the support.

15. The assay of claim 1 wherein the support is in the form of a membrane.

16. The assay of claim 15 wherein the membrane has a thickness of from 250 to 300 microns.

17. The assay of claim 1 wherein the analyte is fixed by immunochemical reaction with a tracer.

18. The assay of claim 1 wherein the support is cellulose acetate modified with a long chain fatty alcohol.

19. The assay of claim 1 wherein the sample is an analyte solution.

20. An assay for determining analyte, comprising:
contacting an amphiphilic cellulose acetate support with sample containing an analyte, said support being essentially free of a binder which recognizes said analyte; fixing analyte on the support; subsequent to the fixing and prior to a subsequent determining of analyte, washing the support to remove proteins and haptens other than analyte fixed on the support; and determining analyte on the support.

21. The assay of claim 20 wherein prior to washing, analyte on the support is contacted with a tracer which binds directly or indirectly to analyte on the support.

22. The assay of claim 21 wherein analyte is fixed on the support by immunobinding to the tracer.

23. The assay of claim 22 wherein the analyte is a protein.

24. The assay of claim 20 wherein the cellulose acetate is modified with a long chain fatty alcohol.

25. The assay of claim 20 wherein the support is in the form of a membrane.

26. The assay of claim 25 wherein the support has a porosity of from 300 to 3,000 Angstroms.

* * * * *